(12) United States Patent
Kah, Jr.

(10) Patent No.: US 7,916,884 B2
(45) Date of Patent: Mar. 29, 2011

(54) EXTERNAL EAR INSERT FOR HEARING COMPREHENSION ENHANCEMENT

(76) Inventor: Carl L. C. Kah, Jr., North Palm Beach, FL (US)

( * ) Notice: Subject to any disclaimer, the term of this patent is extended or adjusted under 35 U.S.C. 154(b) by 1190 days.

(21) Appl. No.: 10/436,716

(22) Filed: May 12, 2003

(65) Prior Publication Data

US 2003/0231783 A1 Dec. 18, 2003

Related U.S. Application Data

(60) Provisional application No. 60/379,871, filed on May 10, 2002.

(51) Int. Cl.
*H04R 25/00* (2006.01)

(52) U.S. Cl. ......................................... 381/328; 381/322

(58) Field of Classification Search .................. 381/322, 381/324, 328, 330, 380–383; 181/22
See application file for complete search history.

(56) References Cited

U.S. PATENT DOCUMENTS

| | | | | |
|---|---|---|---|---|
| 6,160,895 A | * | 12/2000 | Dupont | 381/322 |
| 6,920,229 B2 | * | 7/2005 | Boesen | 381/380 |

FOREIGN PATENT DOCUMENTS

| | | |
|---|---|---|
| EP | 0 147 940 | 7/1985 |
| EP | 0 227 180 | 7/1987 |
| GB | 1 016 222 | 1/1966 |

* cited by examiner

*Primary Examiner* — Suhan Ni
(74) *Attorney, Agent, or Firm* — Ostrolenk Faber LLP

(57) ABSTRACT

A simple hearing enhancement device that takes the normally adequately loud sound levels and optimizes selective frequency gain of the patient's ear passage to improve speech comprehension.

15 Claims, 3 Drawing Sheets

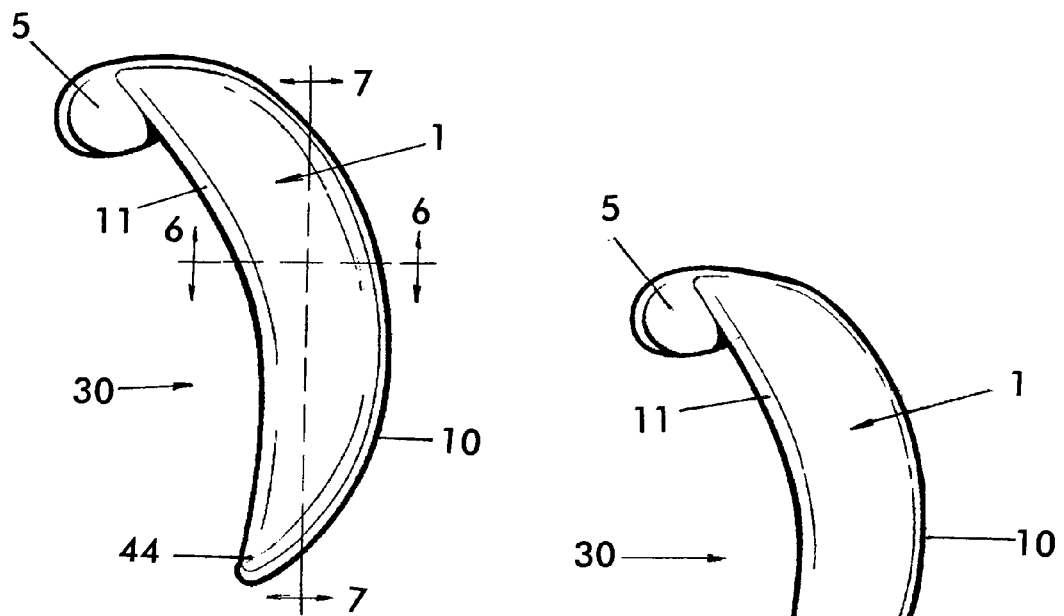
FIG. 4
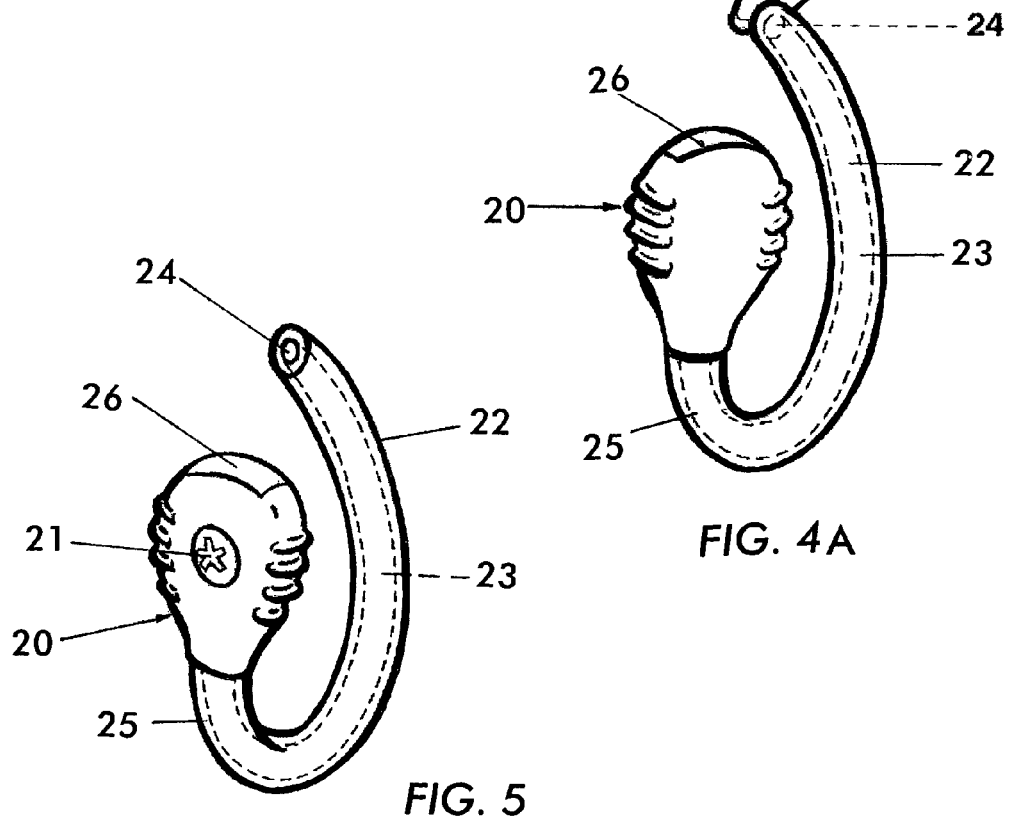
FIG. 4A
FIG. 5

EXTERNAL EAR INSERT FOR HEARING COMPREHENSION ENHANCEMENT

This application claims priority to U.S. Provisional Application Ser. No. 60/379,871, filed May 10, 2002.

TECHNICAL FIELD

The present invention relates a device for hearing enhancement, and more particularly, to a device inserted and attached to the outer ear, which may be used with or without electronic amplification to broadly or selectively enhance hearing ability and comprehension at higher audio frequencies. The invention also relates to a method of enhancing hearing using such a device.

BACKGROUND OF THE INVENTION

There are many devices and much background material pertaining to hearing aids that increase the amplitude of the sound impinging on the eardrum. Some of these operate by bone conduction. These are external amplifying devices which transmit sound through the bones behind the ears. As external devices, they can be unattractive, and can interfere with eyeglasses. Functionally, such devices have the disadvantage of not providing more normal hearing and taking advantage of what adequate hearing a user has.

Most hearing aids have their amplifying transducer fitted into the auditory meatus (the external auditory canal). This blocks the natural amplitude gain at the eardrum (tympanic membrane) produced by the auditory canal and causes substantial or complete amplitude loss so the user must rely totally on electronic amplification.

One problem with such devices is that its is hard to provide frequency band matched amplification electronically to match the patient's hearing where he still has reasonably normal hearing at least at lower frequencies of the natural sound field around him without feedback distortion and over amplification of the background noise. For good or acceptable voice word comprehension, many patients need only some boost at higher frequencies, which is where most of the hearing loss in later life occurs.

In particular, the hearing loss at higher frequencies is often in the range of 30 db or more. Amplification at such levels often results in whistle and feedback. This is generally dealt with by sealing the hearing aid to the wall of the auditory canal, and natural hearing even in the portions of the spectrum for which there is little or no impairment must be foregone. Vent holes are sometimes provided to allow some normal sound field through but there is still substantial attenuation.

As a consequence, many persons with only high frequency hearing impairment find electronic hearing aids to be unsatisfactory, and simply accept the impairment as an unavoidable consequence of aging.

Some passive devices have been considered. Among these are devices constructed in the form or a Helmholtz type resonator cavity box with a small opening and a small exit that was then inserted into the outer ear and ear auditory canal. For various reasons, however, no commercial use has ever been made of such devices.

It is therefore clear that a need exists for an improved hearing enhancement device usable by those with high frequency hearing impairment for whom existing amplified devices are not completely satisfactory.

SUMMARY OF THE INVENTION

The present invention meets this need by means of a passive device which can be inserted in the outer ear or pinna, and used with or without amplification to provide selective or broad-frequency enhanced ear passage gain at high frequencies.

The device is in the form of cup or scoop-shaped member that can be mounted against the back portion of the pinna and is held in place by the surrounding cartilaginous structures. Although the device may project slightly outward from the back portion of the outer ear, the distance is quite small, and the device may be made of a clear relatively flexible plastic material, and is therefore its appearance is not a real impediment to its use.

The device appears to function by tuning the outer auditory passage leading to the eardrum. The shape and position in the outer portion of the pinna relative to the outer end of the auditory passage determines the amplitude and frequency gain response of the auditory passage with the tympanic membrane. By varying its front-to-back and inside-to-outside dimensions, both the peak resonant frequency and the width or sharpness of the resonance can be adjusted. It has been found that such adjustment of the natural resonance frequency response to incoming sound greatly improves speech comprehension, for example, for older individuals whose hearing loss is mainly at higher frequencies rather than across the entire sound spectrum.

Because the device does not block the auditory canal, the passage remains open for normal hearing at the frequency ranges for which there is no impairment. For such persons, amplification may not even be necessary, or if it is, the amplification needed will be considerably less. This avoids the need for very high gain and the consequent sensitivity to feedback which has heretofore required sealing the transducer into the ear.

In fact, since amplification may be not be needed at all times, an amplifying device may be provided in the form of a detachable unit held on the earlobe by a resilient clip with a sound tube that can be fitted into an opening in the earpiece, or electrically connected to a disc speaker element incorporated into the earpiece. This allows the user to remove the amplifier entirely when it is not needed.

The earpiece can be made in various standardized sizes and configurations to provide a range of predetermined response characteristics. The resonant characteristics of an individual's auditory passage, and thus his or her particular need can be determined by placement of a small microphone in the auditory canal and measuring the response to audio excitations from an external speaker at various frequencies and sound levels. One of the standardized earpieces can then be selected in this way Accordingly, a primary object of this invention is to provide a simple passive device for enhancing the speech and other sound comprehension of persons having high frequency hearing impairment.

Another object of the invention is to provide such a device which occupies only a portion of the outer ear, and therefore does not block hearing at lower frequencies for which there is less or no impairment.

It is also an object of the invention is to provide a hearing enhancement device which can be used with or without amplification. A related object is to provide such a device which may be used with an amplifier which provides lower gain that is needed with conventional hearing aids, and therefore is less sensitive to feedback.

A further object of the invention is to provide a method for designing and/or optimizing the selection of an earpiece for overcoming high-frequency hearing impairment.

BRIEF DESCRIPTION OF THE DRAWINGS

FIG. 4 is a side view of the outer surface of a hearing enhancement device for the left ear according to the invention.

FIG. 4A is a pictorial view of the hearing enhancement device for the left ear including a behind the earlobe electronic amplifier or wireless receiver for added selected frequency boost.

FIG. 5 is a pictorial view of the behind the earlobe encapsulated electronic amplifier showing the side opposite that shown in FIG. 4, in which the gain adjustment and battery compartment cover in the flexible leg connected to the hearing enhancement device are visible.

Like parts are given the same reference numeral in all figures.

DETAILED DESCRIPTION OF EMBODIMENTS OF THE INVENTION

Figure 1:
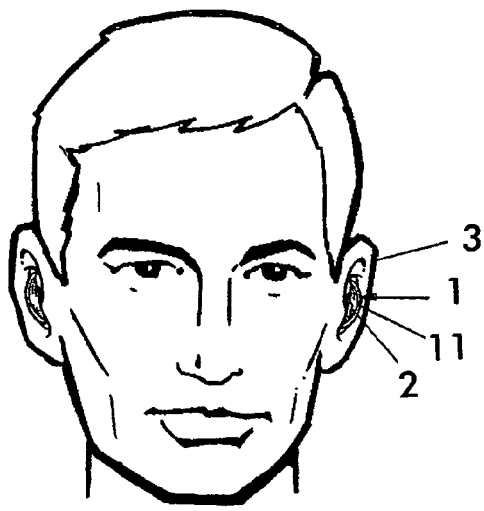
FIG. 1 is a front view of a man's face and head showing the external ear, with hearing enhancement device in place in the external portions of both ears.
Figure 1A:
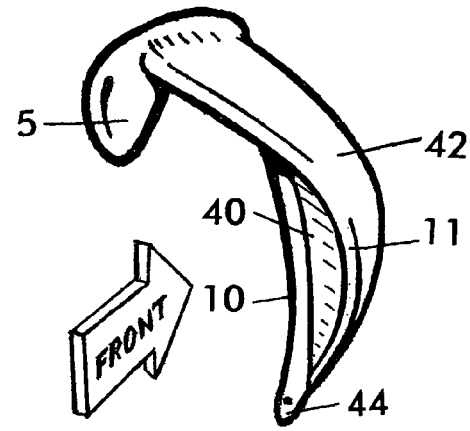
FIG. 1A is a pictorial view of the hearing enhancement device for the left ear.
Figure 2:
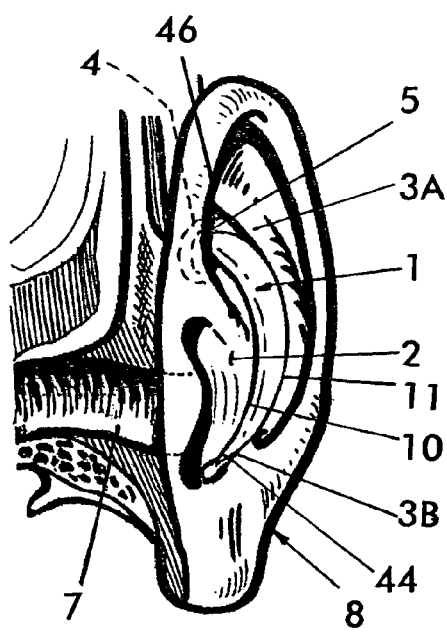
FIG. 2 is a partial cross section of the human ear from the pinna into the auditory canal with a hearing enhancement device according to the invention in the outer ear at the entrance to the auditory canal.

FIG. 1 shows the front view of a man's face and head. Here, earpieces 1 which comprise the hearing enhancement devices according to the invention are positioned in the external portions of both ears 3. As may best be seen in FIGS. 1A, 2, 3, and 4, earpiece 1 is a scoop-like structure having variable three-dimensional curvature in a horizontal plane typified by line 6-6 in FIG. 4, in a vertical plane typified by line 7-7 in FIG. 4, and in the plane of the drawings. As will be appreciated, the earpiece for the left ear has been illustrated. The right earpiece is the mirror image of the left earpiece.

Ear pieces 1 are formed of any suitable or desired plastic material, preferably one which can be made transparent (clear or flesh-toned) and flexible to the desired extent, such as silicone rubber or the like.

Earpiece 1 includes a forwardly facing concave surface 40, and a rearwardly facing convex surface 42, the front edges of which are delimited by forwardly facing edge 11, and outer marginal portions 10 around the outside which is captured by the outer ear cartilage ridge 3A (antihelix). These converge at the bottom end of the earpiece to form a lower tip 44, and also converge at the top where they merge into an upper lug 5. Convex surface 42 is shaped to fit outwardly of the auditory meatus 2 (the opening of the auditory passage) in the concha against the cartilaginous antihelix 3A. Earpiece 1 is held in place by its inherent resiliency, and by lower tip 44 which engages with the lower end 3B of antihelix 3A, and by lug 5 which engages behind the upper end of outer ridge (helix) 46 in a cavity 5. Typically, marginal portion 10 will project slightly beyond antihelix 3A, as best illustrated in FIG. 1. Edge 11 may also project beyond antihelix 3A as well.

As discussed below, it is believed that the curvature and linear dimensions of earpiece 1 provide the high frequency hearing enhancement characteristic of this invention by changing the resonant characteristics of the auditory meatus and outer auditory passage 2. The high frequency enhancement provided by the geometry of earpiece 1 may be entirely sufficient to overcome the hearing deficits of many users under most circumstances. However, if additional enhancement is desired, earpiece 1 can be coupled with an electronic amplifier.

Figure 3:
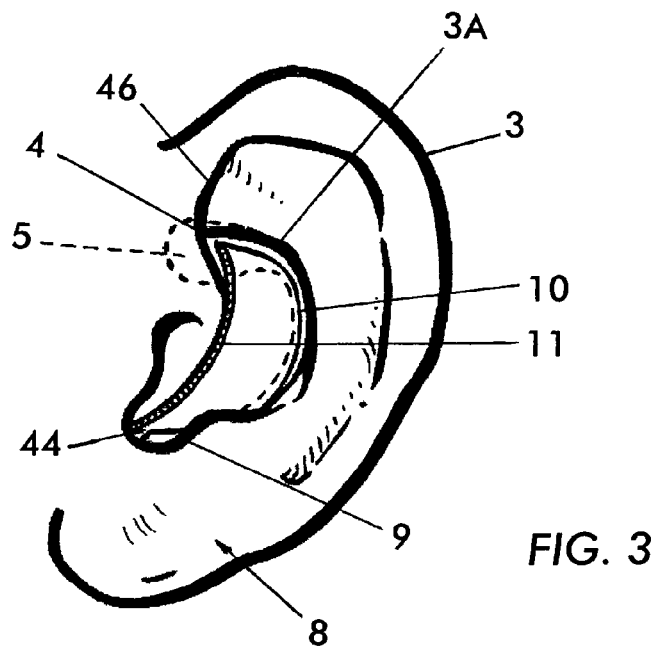
FIG. 3 is a side elevation of the left ear showing the placement of the hearing enhancement device in the pinna.
Figure 3A:
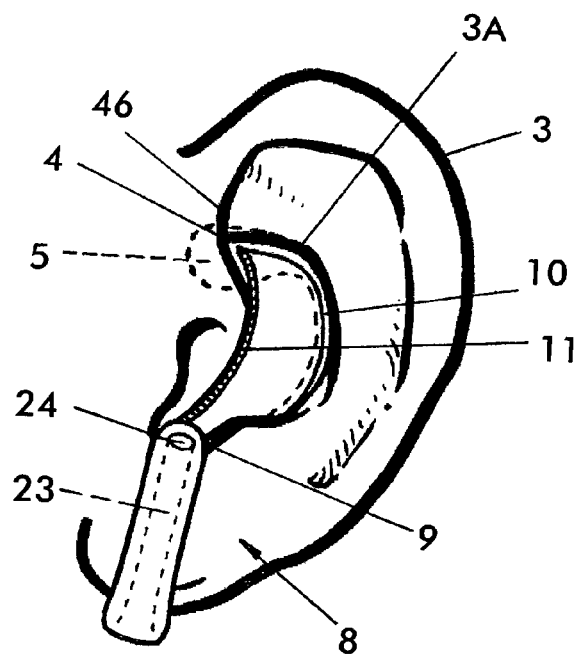
FIG. 3A is a side elevation similar to FIG. 3 which shows the hearing enhancement device coupled to a flexible tab that encapsulates a hearing aid electronic amplifier located behind the earlobe.

FIG. 3A shown how an amplifier unit 20 can be combined with earpiece 1 to form a composite hearing enhancement device 30. A flexible finger 22 attached to the lower end of marginal portion 10 at 9 extends downwardly along ear lobe 8, then bends sidewardly (i.e., toward the upper end of the jaw bone) at its lower end 48, then upwardly again behind earlobe 8. As best illustrated in FIGS. 4A and 5, finger 22 terminates at amplifier unit 20 which is small enough to be substantially hidden behind the earlobe. Finger 22 may itself be sufficiently resilient to hold amplifier unit 20 in place, or may include an embedded resilient member (not shown) to provide the necessary support.

Sound can be coupled from amplifier unit 20 to the auditory meatus 2 in any suitable or desired manner. For example, a transducer (not shown) at the lower end of amplifier housing 50 may be coupled through a passage 23 in flexible finger 22 which terminates in a fitting 24 which passes through opening 9 in earpiece margin 10. The connection between fitting 24 and opening 9 is preferably easily releasable (the connection being provided, for example, by making opening 9 slightly smaller than fitting 24 to take advantage of the resiliency of the earpiece material) so that earpiece 1 can be separated from amplifier unit 20 for cleaning, or when use of the amplifier is not desired or necessary. The sound from passage 23 can be distributed, rather than directed into the ear, by shaping the opening in marginal portion 10, for example, to provide a hollowed-out area around opening 9, if desired.

Alternatively, the transducer my be embedded in the earpiece, and electrically connected to amplifier unit 20 by wires running through passage 23 terminating in a suitable plug connection.

Any suitable commercially available programmable digital type hearing aid amplifier and can be used for this purpose.

Amplifier unit 20 may advantageously be encapsulated with finger 22 as a single unit. As shown in FIG. 5, suitable controls 21 for amplifier unit 20 may be provided in an easily accessible position on the rearwardly facing surface, and a compartment 26 for a suitable battery my be provided in any convenient location.

It has been found that earpiece 1 can be properly sized and shaped to modify the natural resonant characteristics of the users' open auditory canal. In this manner, substantial amplitude gain for higher frequencies at the tympanic membrane can be provided without amplification. This results in improved hearing in general, and in particular, better speech comprehension.

Specifically, by widening or narrowing opening 2 (see FIGS. 1 and 2) along the side of the head, and the length of edge 11 along the head in conjunction with the shape of the earpiece, sound level gain can be provided in auditory canal for the desired frequencies. The distance from marginal portion 10 forward to the auditory canal can be used in conjunction with the curvature of concave surface 40, to broaden or narrow the resonant peak. Both parameters can obviously adjusted in a single device to meet the specific needs of a user.

Alternatively, it appears that a plurality of standardized shapes may be provided in different sizes for large and small ears. Earpieces can designed for frequency gain response at selected frequencies within the lower end of the upper audio spectrum (e.g., approximately 4000-6000 Hz) and for broad or narrow peaking at selected frequencies such as around 4000, 5000, or 6000 Hz. Narrower adjustment (fine tuning) can be obtained by providing either standardized or custom-made inserts for use in conjunction with the standardized earpieces and/or by selective amplification.

Use of standardized earpieces is presently preferred, as will be appreciated by those skilled in the art, since this simplifies and reduces the cost of manufacture, and allows the user to be fitted without having to wait for a custom part to be fabricated.

Auditory canal gain over selected frequency ranges as high as 30 db can be achieved in contrast to 20-30 db attenuation (loss) resulting from insertion of conventional hearing devices into the auditory canal. Since amplification just to overcome that attenuation is not needed, amplification, if needed at all, need only be provided at the higher frequencies, and then, with substantially reduced gain. This, in turn, lessens or avoids the sensitivity to feedback.

In particular, if 10-30 db gain can be obtained by tuning the auditory canal in combination with the earpiece, providing an additional 10-20 db of gain through amplification at selected higher frequencies gives the user a total effective gain of 30-60 db at the ear drum without having to seal the speaker element into the auditory canal. The auditory canal is therefore open to the outside world for more normal hearing of most of the sounds with better speech comprehension.

Since feedback at gain levels below 30 db can be tolerated due to the absorption of surroundings, the limited amplification required substantially eliminates the problem of feedback encountered when the transducer unit is not sealed in the auditory canal.

It has also been found that the earpiece tends to shield the auditory canal from side and back noises to provide better signal to noise characteristic from the front i.e., in the direction the user is looking. This tends to further enhance speech comprehension.

Existing extremely small digital amplifiers can be used which provide multiple adjustable frequency gains to further match the user's hearing loss with reduced amplifier power requirements. An attractive housing such as for an earring can be provided and can even be attached to the ear by a stud extending through a pierced ear lobe. A dummy housing can be provided where amplification is only needed for one ear.

The present invention also comprehends a procedure for designing and optimizing the shape of the earpieces. This is accomplished by placing a very small microphone 1 or 2 millimeters in the auditory canal near the eardrum and then measuring the received signal level of sound amplitude received for various frequencies of sound from a speaker transducer located outside of the ear.

The sound level gain for each frequency can be measured in the auditory canal and the shape of the earpiece adjusted to maximize the sound level gain at the frequencies that give the user the best hearing comprehension of words when tested at various sound levels. Average data can thus be obtained and used to design standardized earpieces with resonance peaks and shapes that can provide best fit on a statistical basis for most users. Tuning for specific user's needs can be provided by standardized or customized inserts for use with the standardized earpieces or by selective amplification.

Although the present invention has been described in relation to particular embodiments thereof, many other variations and modifications and other uses will become apparent to those skilled in the art. It is intended therefore, that the present invention be limited not by the specific disclosure herein, but is to be given the full scope indicated by the appended claims.

What is claimed is:

1. A hearing enhancement device, comprising a shaped earpiece insertable in a user's outer ear, the earpiece being so shaped that it interacts with the user's auditory canal to provide enhanced sound amplitude response as a function of frequency to improve the user's speech comprehension,
   wherein the earpiece further includes:
   a forwardly facing concave first surface;
   a rearwardly facing convex second surface,
   the first and second surfaces converging and joining at upper and lower ends thereof, with terminal elements at the upper and lower ends of the first and second surfaces,
   the earpiece being configured to be held in place in the ear by its inherent resiliency, and by engagement of the terminal elements with cartilaginous portions of the outer ear, and
   so shaped that it provides selective amplitude enhancement of incoming sound to improve a user's speech comprehension.

2. A hearing enhancement device according to claim 1, wherein the terminal element at the lower end is shaped and positioned to engage with the lower end of the antihelix of the ear.

3. A hearing enhancement device according to claim 1, wherein the terminal element at the upper end is shaped and positioned to engage behind the upper end of the helix of the ear.

4. A hearing enhancement device according to claim 3, wherein the terminal element at the upper end is shaped and positioned for insertion in a cavity behind the upper end of helix.

5. A hearing enhancement device according to claim 1, wherein the second surface is shaped and positioned to fit outwardly of the opening of the auditory passage in the concha and against the antihelix.

6. A hearing enhancement device according to claim 1, wherein:
   front edges of the first and second surfaces are delimited by forwardly facing first and second marginal portions,
   the first marginal portion extending more forwardly at a lower end thereof than the second marginal portion, and
   the second marginal portion extending more forwardly at an upper end thereof than the first marginal portion.

7. A hearing enhancement device according to claim 6, wherein the first marginal portion is shaped and dimensioned to project partially beyond the antihelix.

8. A hearing enhancement device according to claim 7, wherein the second marginal portion is shaped and dimensioned to project slightly beyond the antihelix.

9. A hearing enhancement device according to claim 6, wherein the first and second surfaces, and the first and second marginal portions are so shaped and dimensioned that the earpiece interacts with the auditory canal to modify the sound amplitude gain thereof as a function of frequency to provide the selective amplitude enhancement.

10. A hearing enhancement device according to claim 1, wherein the earpiece is so shaped that the amplitude response enhancement is at frequencies of about 4000 Hz and above.

11. A hearing enhancement device according to claim 1, wherein:
   the earpiece is so shaped that the amplitude response enhancement is at frequencies in the range of about 2000 Hz to about 6000 Hz.

12. A hearing enhancement device according to claim 6, wherein:
front edges of the first and second surfaces are delimited by forwardly facing first and second marginal portions, and
the selective amplitude enhancement of the earpiece is frequency dependent according to the shape and positioning of the first and second marginal portions.

13. A hearing enhancement device according to claim 12, wherein the frequency of maximum amplitude enhancement increases or decreases according to the extent that the position of the second marginal portion widens or narrows the effective opening of the auditory canal along the side of the head.

14. A hearing enhancement device according to claim 13, wherein the range of substantial frequency dependent amplitude enhancement increases or decreases according to increases or decreases of the distance from the first marginal portion forward along the head to the auditory canal.

15. A hearing enhancement device according to claim 12, wherein the range of substantial frequency dependent amplitude enhancement increases or decreases according to increases or decreases of the distance from the first marginal portion forward along the head to the auditory canal.

* * * * *